(12) United States Patent
Martin et al.

(10) Patent No.: US 11,107,577 B2
(45) Date of Patent: Aug. 31, 2021

(54) SYSTEM AND METHOD OF UTILIZING DATA OF MEDICAL SYSTEMS

(71) Applicant: Alcon Inc., Fribourg (CH)

(72) Inventors: Peter Martin, Velden (DE); Heiko Bohn, Nuremberg (DE)

(73) Assignee: Alcon Inc., Fribourg (CH)

( * ) Notice: Subject to any disclaimer, the term of this patent is extended or adjusted under 35 U.S.C. 154(b) by 44 days.

(21) Appl. No.: 16/590,104

(22) Filed: Oct. 1, 2019

(65) Prior Publication Data

US 2020/0135332 A1    Apr. 30, 2020

Related U.S. Application Data

(60) Provisional application No. 62/753,277, filed on Oct. 31, 2018.

(51) Int. Cl.
| | |
|---|---|
| *A61B 5/00* | (2006.01) |
| *G16H 40/63* | (2018.01) |
| *A61B 5/145* | (2006.01) |
| *G16H 40/20* | (2018.01) |
| *A61B 5/0205* | (2006.01) |

(Continued)

(52) U.S. Cl.
CPC ............. *G16H 40/40* (2018.01); *G16H 40/63* (2018.01); *G16H 40/67* (2018.01)

(58) Field of Classification Search
CPC ........ G16H 40/67; G16H 40/63; G16H 40/40; G16H 20/17; G06F 3/0482; G06F 3/04842; H04L 67/12; A61B 5/0205; A61B 5/7275
See application file for complete search history.

(56) References Cited

U.S. PATENT DOCUMENTS

| | | | |
|---|---|---|---|
| 10,127,357 B2 * | 11/2018 | Whiting | A61B 5/742 |
| 2014/0142966 A1 * | 5/2014 | Badgett | G06Q 10/0633 705/2 |

(Continued)

FOREIGN PATENT DOCUMENTS

| | | |
|---|---|---|
| EP | 3255478 A1 | 12/2017 |
| WO | 200193756 A2 | 12/2001 |

(Continued)

OTHER PUBLICATIONS

Gia et al., Fault tolerant and scalable IoT-based architecture for health monitoring, 6 pages (Year: 2015).*

*Primary Examiner* — Thuy Dao (57) ABSTRACT

The present disclosure provides a system that may receive first sensor data associated with first multiple measurements of multiple components of multiple medical systems; may receive filter information from first user input; may search, based at least on the filter information, the first sensor data to determine report data; may provide, via a graphical user interface, the report data to a user; may receive second user input that indicates one or more issues associated with at least one of the multiple medical systems; may determine one or more thresholds based at least on the second user input; may receive second sensor data associated with second multiple measurements of the multiple components of the multiple medical systems; and may determine, based at least on the one or more thresholds, at least one of the one or more issues associated with at least one of the multiple medical systems.

20 Claims, 9 Drawing Sheets

FROM FIG. 4A

460 — ISSUE, BASED AT LEAST ON THE AT LEAST ONE OF THE ONE OR MORE ISSUES ASSOCIATED WITH THE AT LEAST ONE OF THE MULTIPLE MEDICAL SYSTEMS, AT LEAST ONE PREVENTATIVE MAINTENANCE ORDER RESPECTIVELY ASSOCIATED WITH THE AT LEAST ONE OF THE MULTIPLE MEDICAL SYSTEMS

465 — ISSUE, BASED AT LEAST ON THE AT LEAST ONE OF THE ONE OR MORE ISSUES ASSOCIATED WITH THE AT LEAST ONE OF THE MULTIPLE MEDICAL SYSTEMS, AT LEAST ONE SERVICE ORDER RESPECTIVELY ASSOCIATED WITH THE AT LEAST ONE OF THE MULTIPLE MEDICAL SYSTEMS (51) Int. Cl.
*G16H 40/40* (2018.01)
*G16H 40/67* (2018.01)

(56) References Cited

U.S. PATENT DOCUMENTS

2014/0180711 A1* 6/2014 Kamen .................. G16H 20/10
　　　　　　　　　　　　　　　　　　　　　　　　705/2
2014/0247154 A1 9/2014 Proud
2015/0154364 A1* 6/2015 Biasi ....................... H04L 45/02
　　　　　　　　　　　　　　　　　　　　　　　　709/223

FOREIGN PATENT DOCUMENTS

WO　　2015074007 A1　5/2015
WO　　2016204937 A1　12/2016

* cited by examiner

SYSTEM AND METHOD OF UTILIZING DATA OF MEDICAL SYSTEMS

BACKGROUND

Field of the Disclosure

This disclosure relates to medical systems utilized in medical procedures and more particularly to utilizing data of the medical systems.

Description of the Related Art

Medical systems can be utilized in medical procedures. A medical system includes sensors that monitor various components of the medical system. The data from the sensors is stored by a computer system of the medical system. A technician that provides service to the medical system can access the computer system of the medical system and the data stored. However, the technician has to travel to a location that utilizes the medical system. This consumes response time if there is an issue associated with the medical system. In one case, there can be a malfunction with the medical system. In another case, there can be a preventative maintenance issue with the medical system. Medical systems can require routine maintenance at various times.

SUMMARY

The present disclosure provides a system able to receive first sensor data associated with first multiple measurements of multiple components of multiple medical systems. In one example, one or more sensors may monitor a laser of a medical system. In a second example, one or more sensors may monitor an amount of energy consumed by a laser of a medical system. In a third example, one or more sensors may monitor an amount of energy produced by a laser of a medical system. In a fourth example, one or more sensors may monitor an amount of gas of a gas container of a medical system. In another example, one or more sensors may monitor how a surgeon utilizes a component of a medical system. A sensor monitoring a component of a medical system may include the sensor measuring physical phenomena. For example, the sensor may provide data based at least on a measurement of the physical phenomena. The system may further receive filter information from first user input. For example, the filter information may be utilized in determining data to report to a user.

The system may further search, based at least on the filter information, the first sensor data to determine report data. For example, the system may search a database, which stores the first sensor data, to determine report data. The system may further provide, via a graphical user interface, the report data to a user. For example, the graphical user interface may be at least a portion of a web-based application. The system may further receive second user input that indicates one or more issues associated with at least one of the multiple medical systems. In one example, an issue associated with at least one of the multiple medical systems may include a maintenance issue. In a second example, an issue associated with at least one of the multiple medical systems may include a preventative maintenance issue. In a third example, an issue associated with at least one of the multiple medical systems may include a malfunction issue. In another example, an issue associated with at least one of the multiple medical systems may include a component impairment issue.

The system may further determine one or more thresholds based at least on the second user input. For example, determining one or more thresholds based at least on the second user input may be based at least on stored sensor data. The system may classify the stored sensor data based at least on the second user input. For example, the system may determine one or more thresholds based at least on one or more classifications of the stored sensor data. The system may further receive second sensor data associated with second multiple measurements of the multiple components of the multiple medical systems. In one example, the system may continue to receive sensor data from the multiple medical systems. In another example, the system may receive sensor data from additional multiple medical systems. The system may further determine, based at least on the one or more thresholds, at least one of the one or more issues associated with at least one of the multiple medical systems. For example, the system may determine at least one of the one or more issues associated with at least one of the multiple medical systems from the second sensor data associated with the second multiple measurements, based at least on the one or more determined thresholds.

The system may further issue, based at least on the at least one of the one or more issues associated with the at least one of the multiple medical systems, at least one warning respectively associated with the at least one of the multiple medical systems. For example, issuing the at least one warning may include providing information indicating the at least one warning via a display of the at least one of the multiple medical systems. The at least one warning may be associated with past operation of the at least one of the multiple medical systems by at least one medical personnel. For example, the at least one warning may be associated with past operation of a medical system by a surgeon. The system may further issue, based at least on the at least one of the one or more issues associated with the at least one of the multiple medical systems, at least one preventative maintenance order respectively associated with the at least one of the multiple medical systems. The system may further issue, based at least on the at least one of the one or more issues associated with the at least one of the multiple medical systems, at least one service order respectively associated with the at least one of the multiple medical systems.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) receive first sensor data associated with first multiple measurements of multiple components of multiple medical systems; ii) store the first sensor data via a database; iii) receive filter information from first user input; iv) search, based at least on the filter information, the first sensor data to determine report data; v) provide, via a graphical user interface, the report data to a user; vi) receive second user input that indicates one or more issues associated with at least one of the multiple medical systems; vii) determine one or more thresholds based at least on the second user input; viii) receive second sensor data associated with second multiple measurements of the multiple components of the multiple medical systems; ix) determine, based at least on the one or more thresholds, at least one of the one or more issues associated with at least one of the multiple medical systems;

x) issue, based at least on the at least one of the one or more issues associated with the at least one of the multiple medical systems, at least one warning respectively associated with the at least one of the multiple medical systems; and xi) issue, based at least on the at least one of the one or more issues associated with the at least one of the multiple medical systems, at least one preventative maintenance order respectively associated with the at least one of the multiple medical systems.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

A surgeon may perform a medical procedure utilizing a medical system. For example, the medical procedure may be or include a surgery involving an eye of a patient. The surgery involving the eye of the patient may be or include a laser eye surgery. The laser eye surgery may be or include a laser vision correction (e.g., laser-assisted in situ keratomileusis (LASIK)). In one example, the medical system may control utilization of one or more medical instruments. In another example, the medical system may record utilization of the one or more medical instruments.

A computer system of the medical system may monitor sensors of the medical system. The computer system may receive and may store data from the sensors of the medical system. The computer system may store the data locally. The computer system may provide the data to another computer system. For example, the computer system may provide the data to a data center. The data center may be or may form part of a cloud computing solution and/or a cloud data storage solution.

The data may be analyzed. For example, the data may be analyzed to determine one or more issues. The one or more issues may include a deficient surgical technique, an inexperienced surgical technique, and/or one or more maintenance issues of one or more components of the medical system, among others. In one example, determining a level of skill in utilizing the medical system may be utilized in determining if an issue exists with the medical system. In a second example, one or more maintenance issues of one or more components of the medical system may include one or more preventative maintenance issues. In a third example, one or more maintenance issues of one or more components of the medical system may include one or more routine maintenance issues. In another example, one or more maintenance issues of one or more components of the medical system may include one or more malfunctions and/or one or more impairments associated with one or more components of the medical system.

One or more computer systems may be configured to utilize the data from the sensors of a medical system to determine one or more issues. For example, one or more computer systems may be configured to learn from the data from the sensors of a medical system to determine one or more issues. The one or more computer systems may be trained to determine one or more issues. For example, the one or more computer systems may be trained by the data from the sensors of a medical system and by user responses to the data from the sensors of the medical system. The one or more computer system may be trained to perform one or more actions. For example, the one or more computer systems may correlate data from sensors of a medical system and perform one or more actions based on the correlated data. The one or more action may include preventative and/or predictive maintenance. For example, the one or more computer systems may issue service orders in performing the preventative and/or predictive maintenance. A technician may receive a service order to complete a physical portion of the preventative and/or predictive maintenance.

Figure 1:
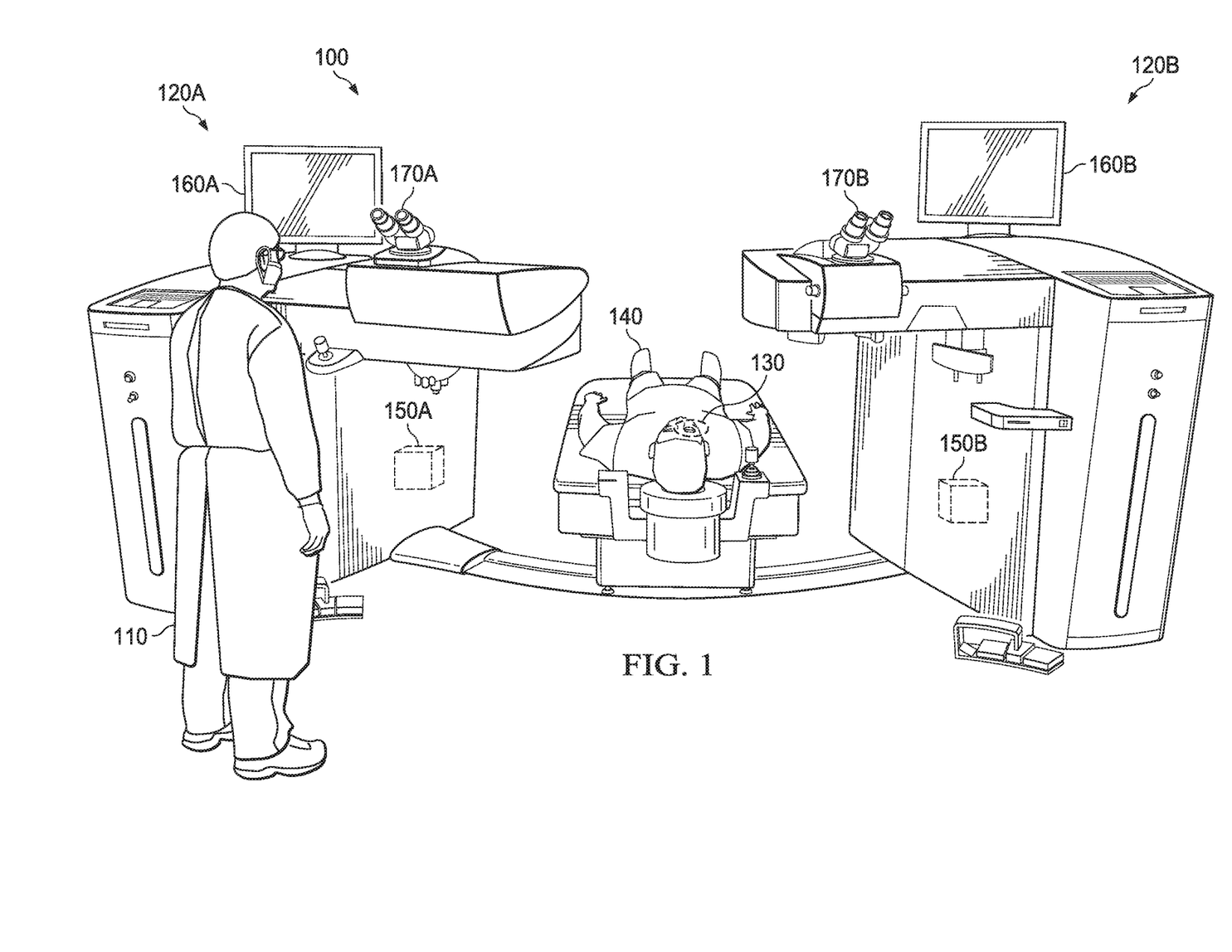
FIG. 1 illustrates an example of a system.

Turning now to FIG. 1, an example of a system is illustrated. As shown, a surgeon 110 may utilize a system 100. For example, surgeon 110 may utilize system 100 in a surgery involving a patient portion 130 of a patient 140. System 100 may include multiple systems. As shown, system 100 may include a cutting system 120A. For example, surgeon 110 may utilize system 120A in cutting patient portion 130. Patient portion 130 may include a flap in a cornea of an eye of patient 140. As illustrated, system 100 may include a shaping system 120B. For example, surgeon 110 may utilize shaping system 120B in performing ablation on an interior part of the cornea of patient 140.

As shown, system 120A may include a display 160A. As illustrated, system 120A may include a microscope display 170A. For example, microscope display 170A may include a microscope integrated display (MID). As shown, system 120B may include a display 160B. As illustrated, system 120B may include a microscope display 170B. For example, microscope display 170B may include a MID.

System 120A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 160A and 170A, along with control devices and a computer system 150A. As shown, system 120A may include computer system 150A.

Systems 120A and 120B may be physically separated as shown in FIG. 1. Patient 140 may be moved between systems 120A and 120B. Alternatively, patient 140 may remain stationary and systems 120A and 120B may be moved to patient 140. Systems 120A and 120B may be physically combined into a single unitary device, such that neither the device nor patient 140 is repositioned when switching between systems 120A and 120B.

System 100 may include one or more control devices for controlling systems 120A and 120B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 100 may include includes at least one computer system configured to generate an image presented on at least one of displays 160A, 170A, 160B, and 170B, among others. For example, the at least one computer system may include one or more of computer systems 150A and 150B. One or more of computer systems 150A and 150B may be coupled to observational devices, such as a microscope, a camera, an optical coherence tomography (OCT) device or display, or another device able to measure the position of the eye undergoing surgery. One or more of computer systems 150A and 150B may be coupled to one or more of the control devices.

In one example, cutting device computer system 150A: i) may be coupled to observational devices that observe the eye when patient 140 is positioned with system 120A, ii) may provide graphical information regarding the planned flap location and the planned area of ablation to one or more of displays 60A and 170A, and iii) may be coupled to one or more control devices of system 120A. In a second example, shaping device computer 150B: i) may be coupled to observational devices that observe the eye when patient 140 is positioned with shaping device 130, ii) may provide graphical information regarding the planned flap location and the planned area of ablation to one or more of displays 60B and 170B, and iii) may be coupled to one or more control devices of system 120B. In another example, a computer system may include the properties and/or the attributes described above with respect to computer systems 150A and 150B.

A computer system of system 100 may be coupled to another part of system 100 in a wired fashion or in a wireless fashion. One of more of computer systems of system 100 may be coupled to a database, stored locally, on a remote computer system or a remote data center, or both that store patient data, treatments plans, or other information associated with medical treatments and/or system 100. In one example, the database may include a relational database. In a second example, the database may include a graph database. In another example, the database may include a "Not Only SQL" (NoSQL) database.

System 100 may enter information regarding a patient and the treatment to be performed on that patient or actually performed on that patient. System 100 may allow a user to enter and view information regarding a patient and the treatment to be performed on that patient. Such data may include information about the patient, such as identifying information, the patient's medical history, and information about patient portion 130 being treated. Such data may include information about the treatment plans, such as the shape and location of a corneal cut and a location and a degree of corneal ablation, among others.

Figure 2A:
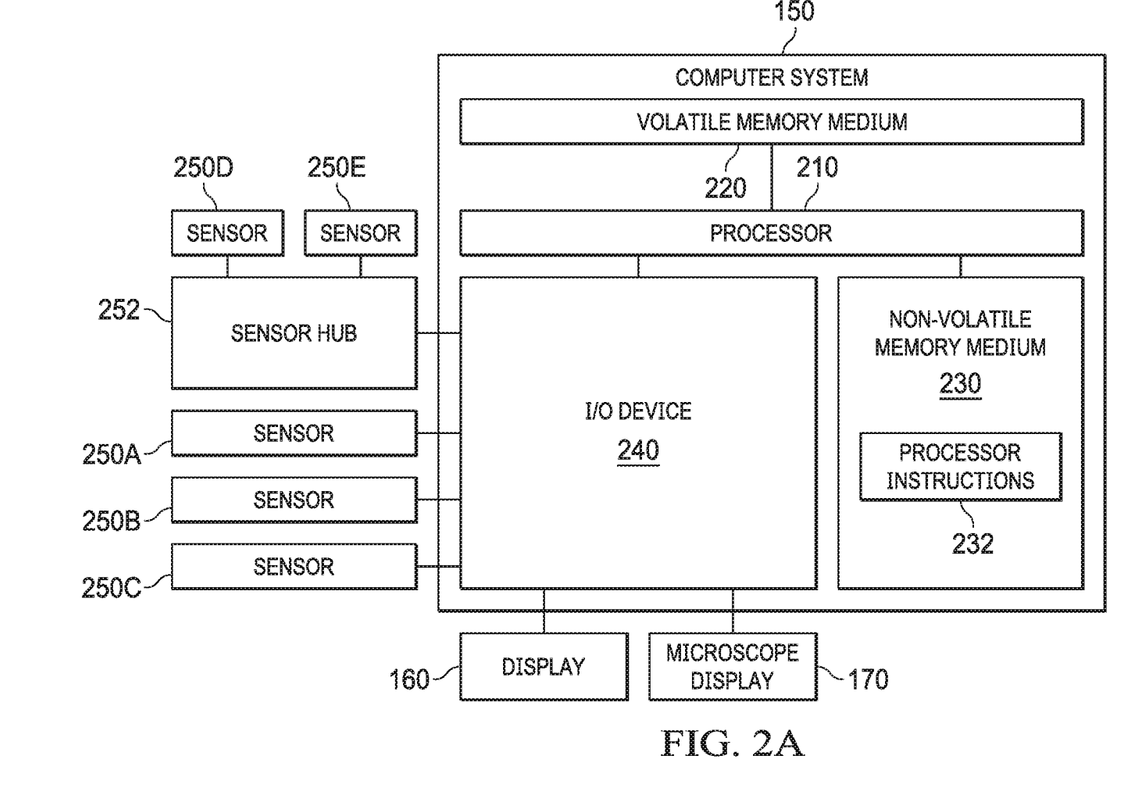
FIG. 2A illustrates an example of a computer system.

Turning now to FIG. 2A, an example of a computer system is illustrated. As shown, computer system 150 may include a processor 210, a volatile memory medium 220, a non-volatile memory medium 230, and an input/output (I/O) device 240. As illustrated, volatile memory medium 220, non-volatile memory medium 230, and I/O device 240 may be communicatively coupled to processor 210.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 230 may include processor instructions 232. Processor instructions 232 may be executed by processor 210. In one example, one or more portions of processor instructions 232 may be executed via non-volatile memory medium 230. In another example, one or more portions of processor instructions 232 may be executed via volatile memory medium 220. One or more portions of processor instructions 232 may be transferred to volatile memory medium 220.

Processor 210 may execute processor instructions 232 in implementing at least a portion of one or more systems, one or more flow charts, one or more processes, and/or one or more methods described herein. For example, processor instructions 232 may be configured, coded, and/or encoded with instructions in accordance with at least a portion of one or more systems, one or more flowcharts, one or more methods, and/or one or more processes described herein. Although processor 210 is illustrated as a single processor, processor 210 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 210 may include any suitable system, device, or apparatus operable to interpret and execute program instructions, process data, or both stored in a memory medium and/or received via a network. Processor 210 further may include one or more microprocessors, microcontrollers, digital signal processors (DSPs), application specific integrated circuits (ASICs), or other circuitry configured to interpret and execute program instructions, process data, or both.

I/O device 240 may include any instrumentality or instrumentalities, which allow, permit, and/or enable a user to interact with computer system 150 and its associated components by facilitating input from a user and output to a user. Facilitating input from a user may allow the user to manipulate and/or control computer system 150, and facilitating output to a user may allow computer system 150 to indicate effects of the user's manipulation and/or control. For example, I/O device 240 may allow a user to input data, instructions, or both into computer system 150, and otherwise manipulate and/or control computer system 150 and its associated components. I/O devices may include user interface devices, such as a keyboard, a mouse, a touch screen, a joystick, a handheld lens, a tool tracking device, a coordinate input device, or any other I/O device suitable to be used with a system, such as system 100.

I/O device 240 may include one or more busses, one or more serial devices, and/or one or more network interfaces, among others, that may facilitate and/or permit processor 210 to implement at least a portions of one or more systems, processes, and/or methods described herein. In one example, I/O device 240 may include a storage interface that may facilitate and/or permit processor 210 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 240 may include a network interface that may facilitate and/or permit processor 210 to communicate with a network. I/O device 240 may include one or more of a wireless network interface and a wired network interface. In a third example, I/O device 240 may include one or more of a peripheral component interconnect (PCI) interface, a PCI Express (PCIe) interface, a serial peripheral interconnect (SPI) interface, and an inter-integrated circuit ($I^2C$) interface, among others. In another example, I/O device 240 may facilitate and/or permit processor 210 to communicate data with one or more of display 160 and microscope display 170, among others.

As shown, I/O device 240 may be communicatively coupled to display 160 and microscope display 170. For example, computer system 150 may be communicatively coupled to display 160 and microscope display 170 via I/O device 240. I/O device 240 may facilitate and/or permit processor 210 to communicate data with one or more elements of microscope display 170.

As illustrated, I/O device 240 may be coupled to sensors 250A-250C. For example, a sensor 250 may measure physical phenomena associated with a component of system 100. A sensor 250 may transform a measurement physical phenomena associated with a component of system 100 into digital data. As shown, I/O device 240 may be coupled to a sensor hub 252. As illustrated, sensor hub 252 may be coupled to sensors 250D and 250E. For example, sensor hub 252 may receive data from sensors 250D and 250E and may provide the data from sensors 250D and 250E to I/O device 240. Sensor hub 252 may aggregate data from sensors 250D and 250E and may provide aggregated data from sensors 250D and 250E to I/O device 240. Sensor hub 252 may receive data from sensors 250D and 250E via first protocol and provide the data from sensors 250D and 250E to I/O device 240 via a second protocol, different from the first protocol. Sensor hub 252 may include a microcontroller.

Figure 2B:
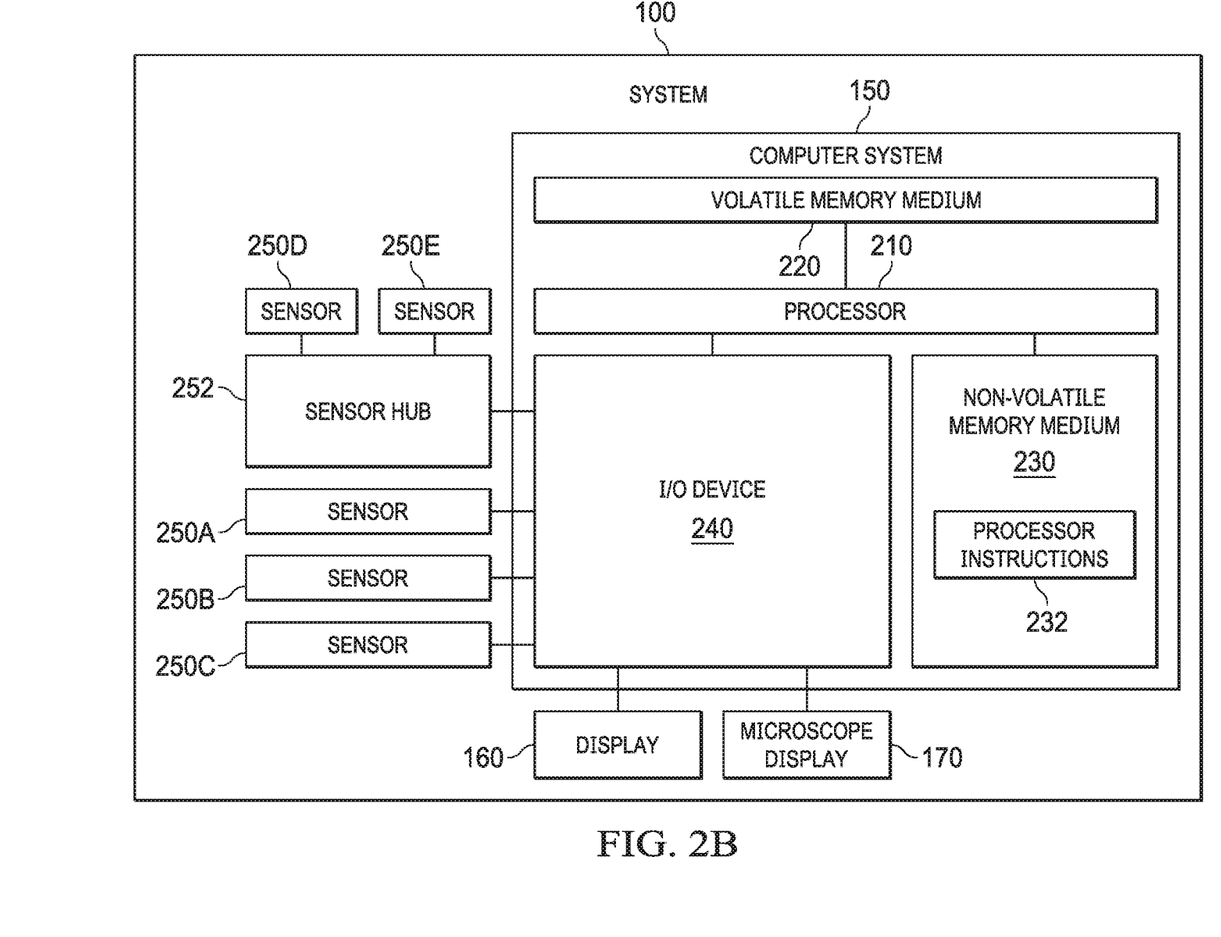
FIG. 2B illustrates another example of a system.

Turning now to FIG. 2B, an example of a system is illustrated. As shown, system 100 may include computer system 150, display 160, microscope display 170, sensors 250A-250E, and sensor hub 252. One or more of sensors 250A-250E may receive information associated with one or more components of system 100. The information associated with one or more components of system 100 may be utilized in determining one or more states of system 100. The information associated with one or more components of system 100 may be utilized in determining one or more issues associated with system 100.

In one example, one or more sensors 250 may monitor a laser of system 100. In a second example, one or more sensors 250 may monitor an amount of energy consumed by a laser of system 100. In a third example, one or more sensors 250 may monitor an amount of energy produced by a laser of system 100. In a fourth example, one or more sensors 250 may monitor an amount of gas of a gas container of system 100. In another example, one or more sensors may monitor how surgeon 110 utilizes a component of system 100.

System 100 may store data from one or more sensors 250 locally. For example, computer system 150 may store data from one or more sensors 250 locally. System 100 may store data from one or more sensors 250 remotely. For example, computer system 150 may provide data from one or more sensors to a remote computer system.

Figure 2C:
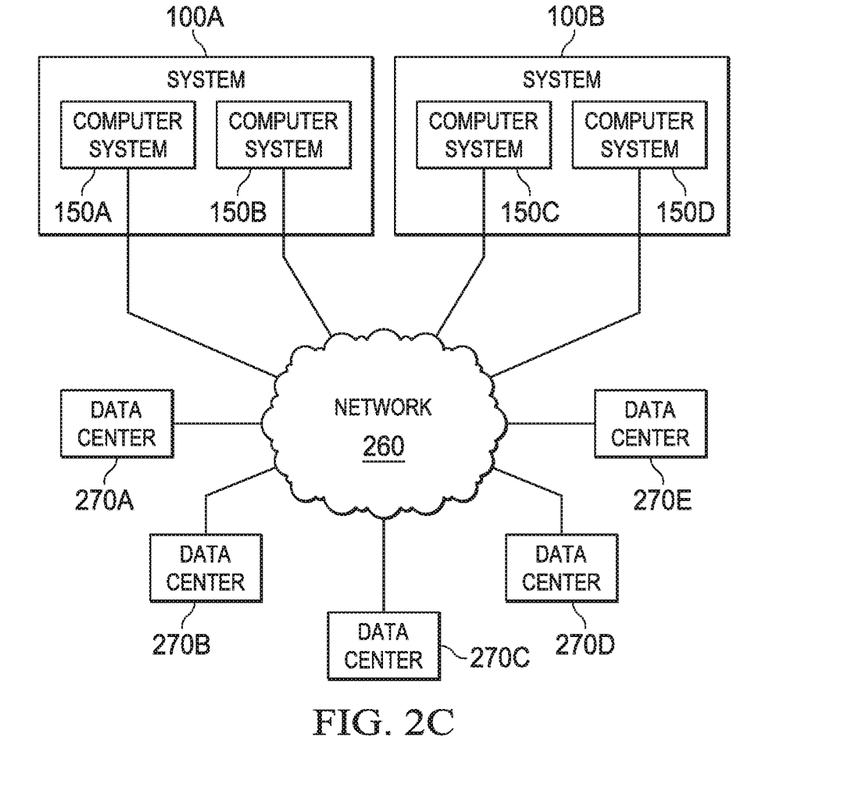
FIG. 2C illustrates an example of computer systems and data centers.

Turning now to FIG. 2C, an example of computer systems and data centers are illustrated. As shown, computer systems 150A-150D may be coupled to a network 260. As illustrated, data centers 270A-270E may be coupled to network 260. A data center 270 may include one or more computer systems. For example, a computer of a data center 270 may include one or more structures and/or one or more functionalities as those described with reference to computer system 150. One or more of computer systems 150A-150D may provide data to one or more of data centers 270A-270E via network 260. For example, one or more of computer systems 250A-250D may provide data from one or more sensors 250 to one or more of data centers 270A-270E via network 260. One or more of computer systems 150A-150D may provide data to one or more of data centers 270A-270E via network 260 in an encrypted fashion. In one example, a computer system 150 may encrypt data from one or more sensors 250 and may provide encrypted data to one or more of data centers 270A-270E via network 260. In another example, a computer system 150 may encrypt data associated with a treatment and may provide encrypted data to one or more of data centers 270A-270E via network 260. One or more of computer systems 150A-150D may receive data from one or more of data centers 270A-270E via network 260.

Network 260 may include a wired network, a wireless network, an optical network, or a combination of the foregoing, among others. Network 260 may include and/or be coupled to various types of communications networks. For example, network 260 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

One or more of data centers 270A-270E may store data from one or more of computer systems 150A-150D, among others. One or more of data centers 270A-270E may store data from one or more of sensors 250A-250E, among others. One or more of data centers 270A-270E may store data via a database. In one example, the database may include a relational database. In a second example, the database may include a graph database. In another example, the database may include a NoSQL database. One or more of data centers 270A-270E may be utilized in implementing a cloud computing solution. In one example, one or more computer systems of one or more of data centers 270A-270E may be utilized in implementing a cloud computing solution. In another example, one or more virtual machines of one or more computer systems of one or more of data centers 270A-270E may be utilized in implementing a cloud computing solution. One or more of data centers 270A-270E may be utilized in implementing a cloud data storage solution. In one example, a cloud data storage solution may store data from one or more of computer systems 150A-150D, among others. In another example, a cloud data storage solution may store data from one or more of sensors 250A-250E, among others. A cloud data storage solution may store data via a database. In one example, the database may include a relational database. In a second example, the database may include a graph database. In another example, the database may include a NoSQL database.

Figure 3A:
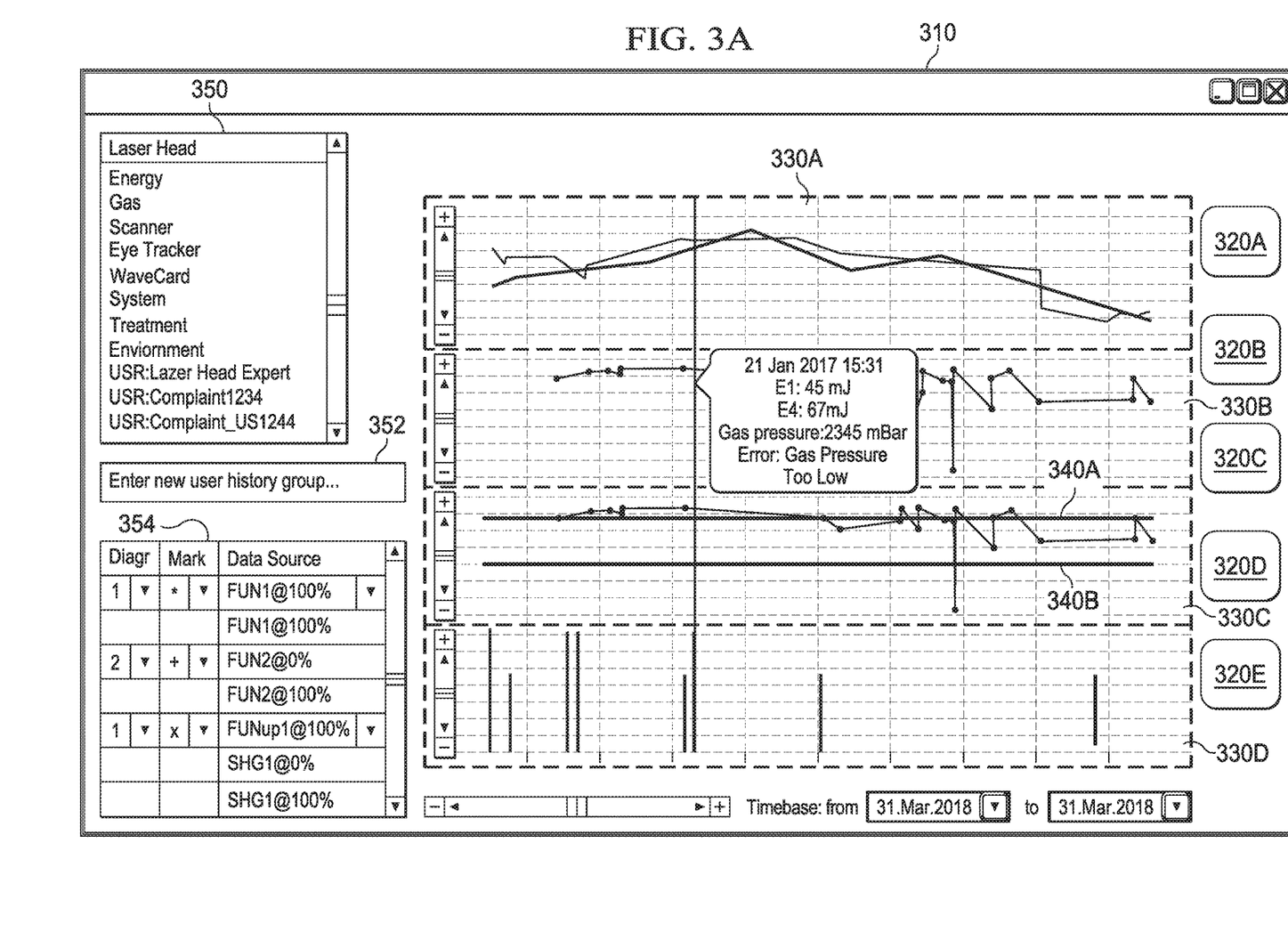
FIG. 3A illustrates an example of a graphical user interface.
Figure 3B:
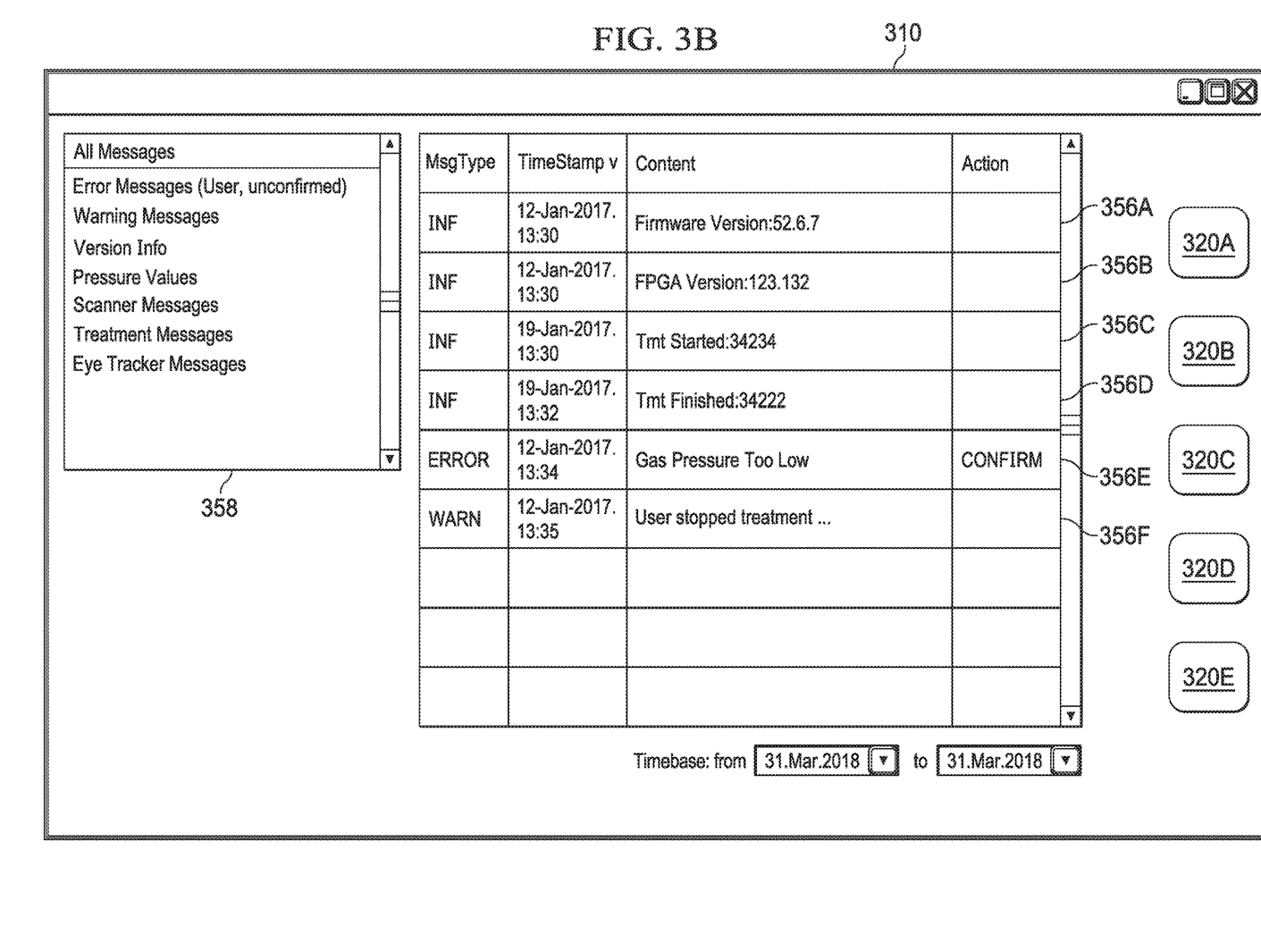
FIG. 3B illustrates a second example of a graphical user interface.

Turning now to FIG. 3A, an example of a graphical user interface is illustrated. As shown, a graphical user interface (GUI) 310 may include icons 320A-320E. An icon of 320A-320E may be selected. In one example, icon 320A may be selected to select a system 100. After icon 320A is selected, system 100A, system 100B, etc. may be selected. A medical facility may be associated with a system 100. In a second example, icon 320B may be selected to view treatment data. FIG. 3B illustrates an example GUI 310 displaying treatment data. In a third example, icon 320C may be selected to select one or more log files. The one or more log files may include data from one or more sensors 250. In a fourth example, icon 320D may be selected to download the one or more log files. In another example, icon 320E may be selected to delete a history group.

As illustrated, GUI areas 330A-330D may present data. In one example, GUI areas 330A-330D may provide report data. The report data may be generated from a search based at least on filter information. In another example, the data presented may be from system 100. The data presented may be from one or more sensors 250 of system 100. In one example, GUI area 330 may present data from a sensor 250 of system 100. In another example, GUI area 330 may present data from multiple sensors 250 of system 100. As shown, GUI area 330C may include thresholds 340A and 340B. For example, a threshold 340 may be configured. A threshold 340 may be configured from user input. As illustrated, data points may be plotted outside thresholds 340A and 340B. In one example, data points may be plotted outside thresholds 340A and 340B may indicate one or more issues associated with system 100. In another example, data points may be plotted outside thresholds 340A and 340B may indicate one or more issues associated with surgeon 110.

As shown, GUI 310 may include a selection menu 350. For example, selection menu 350 may include history groups. A history group may be selected in categorizing data from sensors 250 of system 100. In the example illustrated, a history group of "Laser Head" may have been selected. As illustrated, GUI 310 may include a text input box 352. For example, text input box 352 may be utilized to input text. As shown, GUI 310 may include dropdown menus 354. For example, a dropdown menu may be selected. A selected dropdown menu may indicate data to be presented via a GUI area 330.

GUI 310 may include a web browser. For example, GUI 310 may include a front-end to a web-based application. The web-based application may be implemented via one or more computer systems of one or more data centers 270. The web-based application may be implemented via a cloud computing solution.

GUI 310 may be utilized by a user to monitor a system 100. For example, system 100 may include numerous sensors that provide data associated with system 100. GUI 310 may provide the data associated with system 100 in a fashion that may be discernable by the user. In one example, the user may discern one or more issues associated with system 100. The data associated with system 100 may be correlated with one or more issues associated with system 100. In another example, the user may discern one or more issues associated with surgeon 110. The data associated with system 100 may be correlated with one or more issues associated with surgeon 110.

An artificial intelligence (AI) may utilize data from sensors 250. The AI may learn based at least on data from sensors 250 and based at least on a response of a user to the data from sensors 250. For example, the AI learning may be supervised based at least on the data from sensors 250 and based at least on the response of the user to the data from sensors 250. After the AI learns, the AI may determine one or more issues associated with a system 100 and/or a surgeon 110. The AI may provide information based at least on the one or more issues associated with a system 100 and/or a surgeon 110. For example, the information provided by the AI may include one or more alerts associated with the one or more issues.

The AI may perform one or more actions based at least on the one or more issues associated with a system 100 and/or a surgeon 110. In one example, the AI may issue a service order associated with a system 100. In a second example, the AI may issue a preventative maintenance order associated with a system 100. In a third example, the AI may issue a warning associated with a system 100. In another example, the AI may cease operations of one or more components of a system 100.

Turning now to FIG. 3B, a second example of a graphical user interface is illustrated. As shown, GUI 310 may include icons 320A-320E. As illustrated, GUI 310 may include messages 356A-356F. For example, a message 356 may be associated with a medical treatment. The medical treatment may have been provided in association with a system 100. As shown, GUI 310 may include a message categorization menu 358. For example, GUI 310 may display messages based at least on a message category selected from message categorization menu 358.

Figure 3C:
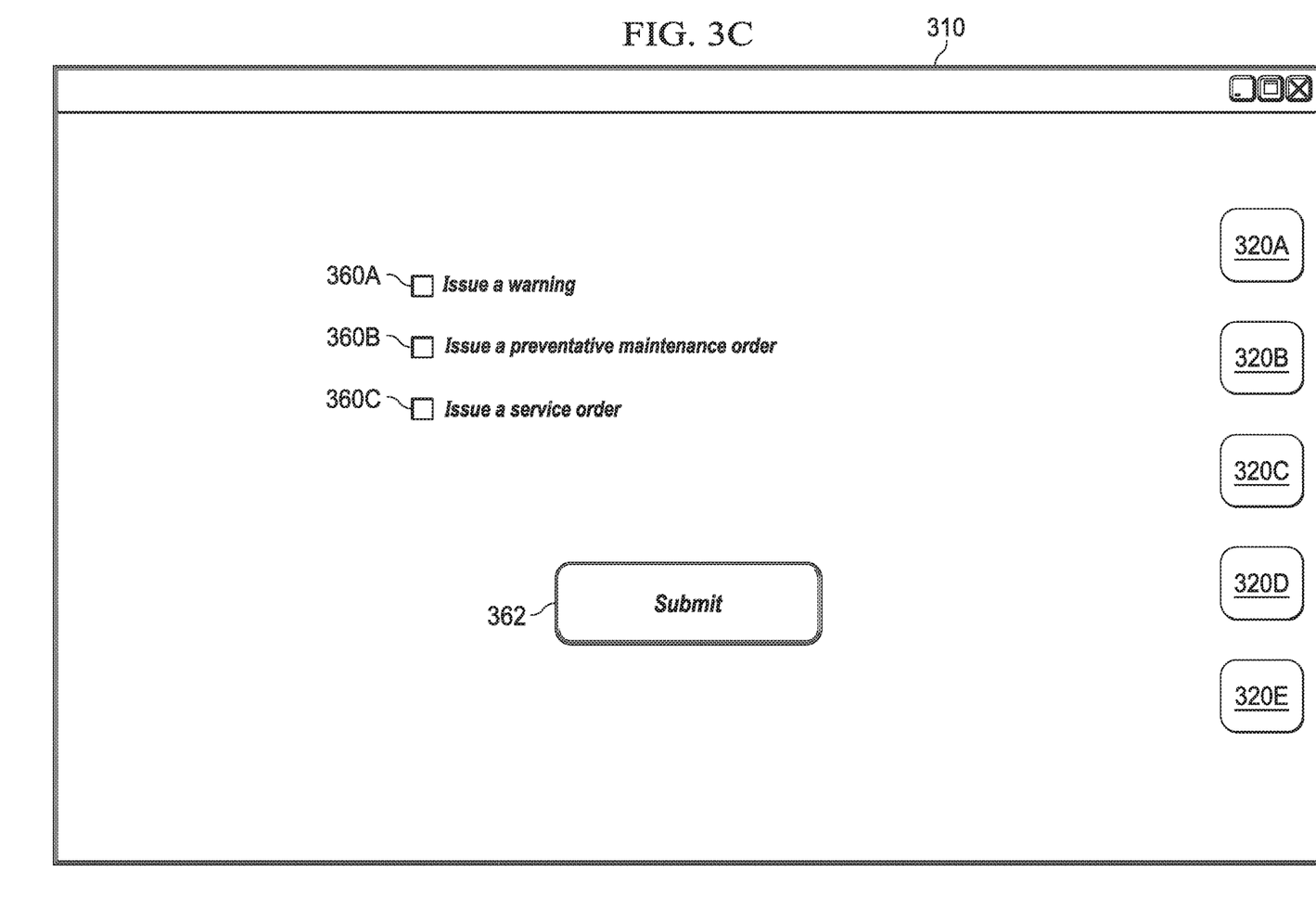
FIG. 3C illustrates another example of a graphical user interface.

Turning now to FIG. 3C, another example of a graphical user interface is illustrated. As illustrated, GUI 310 may include selection areas 360A-360C. For example, selection areas 360A-360C may be check boxes. A user may select selection area 360A to issue a warning associated with a system 100. A user may select selection area 360B to issue a preventative maintenance order associated with a system 100. A user may select selection area 360C to issue a service order associated with a system 100. A user may select a submit icon 362 to execute an issuance associated with one or more of selected selection areas 360A-360C.

One or more thresholds may be determined based at least on one or more of selected selection areas 360A-360C. For example, report data may be correlated with the at least on one or more of selected selection areas 360A-360C to determine one or more thresholds. An AI may correlate the report data with the at least on one or more of selected selection areas 360A-360C to determine one or more thresholds. For example, the AI may correlate the report data with the at least on one or more of selected selection areas 360A-360C to determine one or more thresholds of sensor data. The AI may learn from user input to determine one or more thresholds of sensor data. For example, the AI may learn from user input to determine one or more thresholds of sensor data and what one or more actions to take in response to the sensor data in relation to the one or more thresholds. For example, the AI may utilize supervised machine learning to determine one or more thresholds of sensor data and what one or more actions to take in response to the sensor data in relation to the one or more thresholds.

Figure 4A:
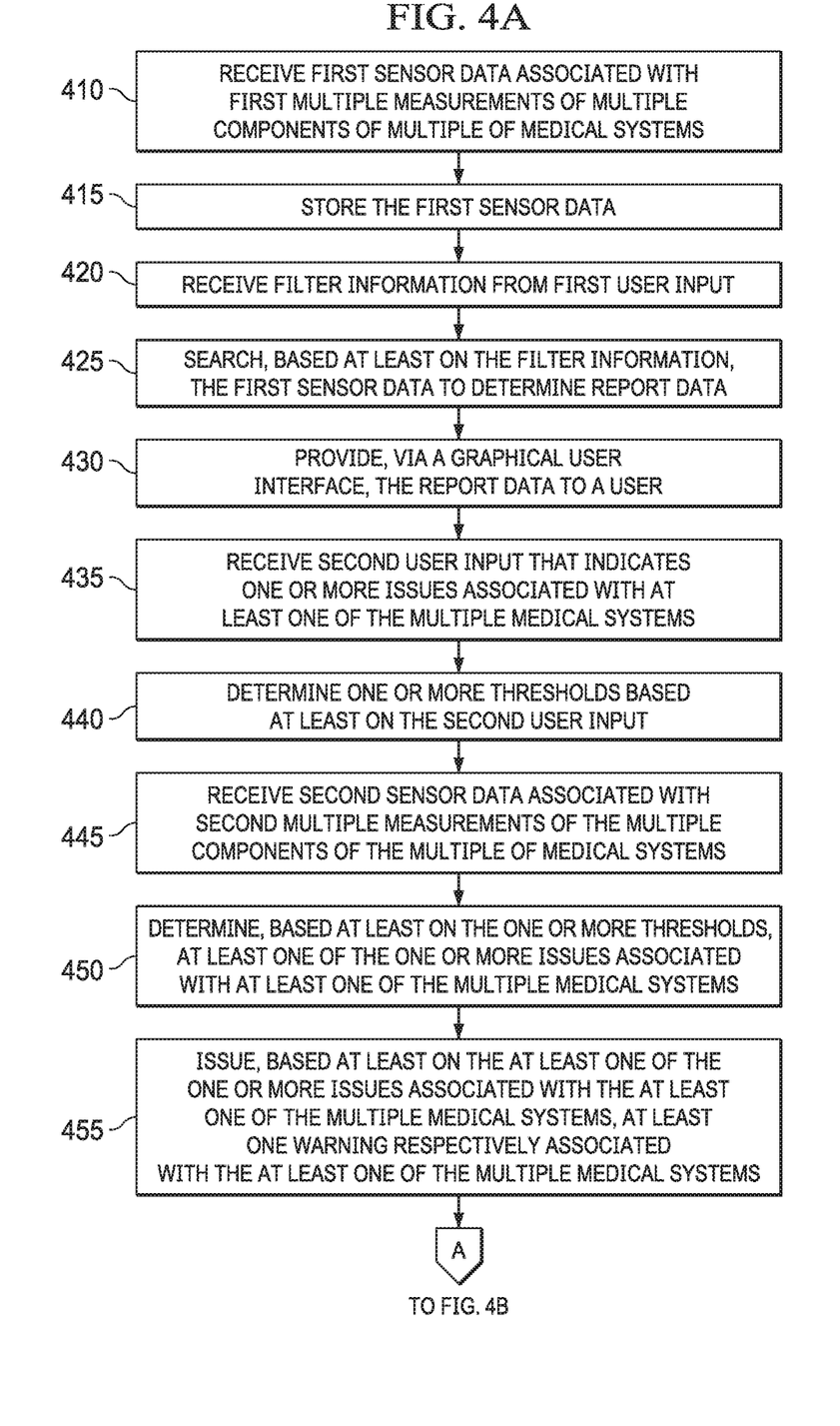
FIGS. 4A and 4B illustrate an example of a method of operating a system.
Figure 4B:
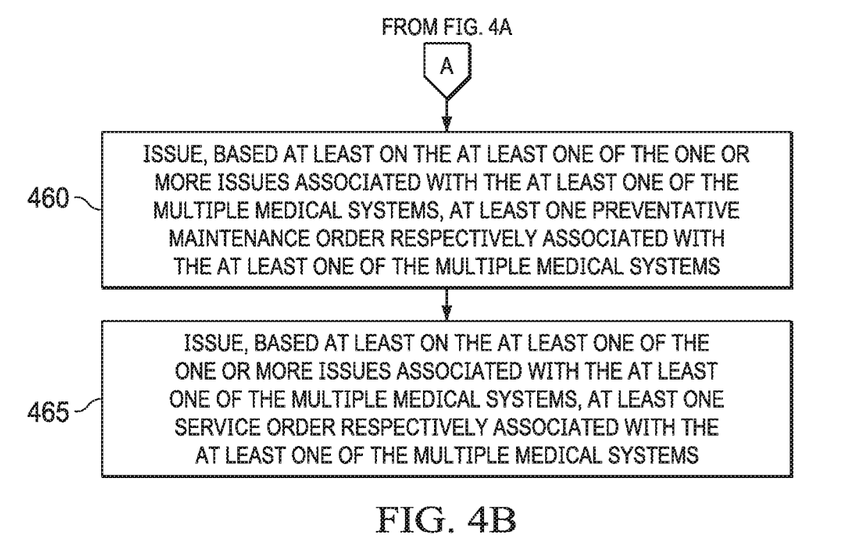

Turning now to FIGS. 4A and 4B, an example of a method of operating a system is illustrated. At 410, first sensor data associated with first multiple measurements of multiple components of multiple of medical systems may be received. In one example, receiving first sensor data associated with first multiple measurements of multiple components of multiple of medical systems may include a data center receiving the first sensor data associated with the first multiple measurements of the multiple components of the multiple of medical systems. In another example, receiving first sensor data associated with first multiple measurements of multiple components of multiple of medical systems may include one or more computer systems of a data center receiving the first sensor data associated with the first multiple measurements of the multiple components of the multiple of medical systems.

At 415, the first sensor data may be stored. For example, the first sensor data may be stored in a database. At 420, filter information may be received from first user input. For example, filter information may be received from first user input via a graphical user interface. At 425, the first sensor data may be searched, based at least on the filter information, to determine report data. For example, searching, based at least on the filter information, the first sensor data to determine the report data may include searching the database to determine the report data.

At 430, the report data may be provided, via a graphical user interface, to a user. For example, providing, via the graphical user interface, the report data to the user may include providing at least a portion of a web-based application to the user. At 435, second user input that indicates one or more issues associated with at least one of the multiple medical systems may be received. At 440, one or more thresholds based at least on the second user input may be determined. At 445, second sensor data associated with second multiple measurements of the multiple components of the multiple medical systems may be received.

At 450, at least one of the one or more issues associated with at least one of the multiple medical systems may be determined based at least on the one or more thresholds. At 455, at least one warning respectively associated with the at least one of the multiple medical systems may be issued based at least on the at least one of the one or more issues associated with the at least one of the multiple medical systems. In one example, issuing the at least one warning respectively associated with the at least one of the multiple medical systems may include providing information indicating the at least one warning via a display of the at least one of the multiple medical systems. In another example, the at least one warning may be associated with past operation of the at least one of the multiple medical systems by at least one medical personnel. The at least one warning may be associated with past operation of system 100 by surgeon 110. In one example, the at least one warning may be provided to surgeon 110 via display 160. In another example, the at least one warning may be provided to surgeon 110 via microscope display 170.

At 460, at least one preventative maintenance order respectively associated with the at least one of the multiple medical systems may be issued based at least on the at least one of the one or more issues associated with the at least one of the multiple medical systems. At 465, at least one service order respectively associated with the at least one of the multiple medical systems may be issued based at least on the at least one of the one or more issues associated with the at least one of the multiple medical systems.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system, comprising:
   at least one processor; and
   a memory medium that is coupled to the at least one processor and that includes instructions, when executed by the at least one processor, cause the system to:
   receive first sensor data associated with a first plurality of measurements of a plurality of components of a plurality of medical systems;
   receive filter information from first user input;
   search, based at least on the filter information, the first sensor data to determine report data;
   provide, via a graphical user interface, the report data to a user, the report data displayed on the graphical user interface, the report data comprising a plot of data points associated with the first sensor data;
   receive second user input that indicates one or more issues associated with at least one of the plurality of medical systems;
   determine one or more thresholds based at least on the second user input;
   display the one or more thresholds on the graphical user interface, the plot of data points associated with the first sensor data displayed with the one or more thresholds;
   receive second sensor data associated with a second plurality of measurements of the plurality of components of the plurality of medical systems;

display a plot of data points associated with the second sensor data on the graphical user interface along with the one or more thresholds;

determine, based at least on the one or more thresholds, at least one of the one or more issues associated with at least one of the plurality of medical systems, at least one of the plotted data points associated with the first sensor data located outside the one or more thresholds indicating an issue with at least one of the plurality of medical systems; and issue, based at least on the at least one of the one or more issues associated with the at least one of the plurality of medical systems, at least one warning respectively associated with the at least one of the plurality of medical systems.

2. The system of claim 1, wherein the instructions further cause the system to:

issue, based at least on the at least one of the one or more issues associated with the at least one of the plurality of medical systems, at least one preventative maintenance order respectively associated with the at least one of the plurality of medical systems.

3. The system of claim 1, wherein the instructions further cause the system to:

issue, based at least on the at least one of the one or more issues associated with the at least one of the plurality of medical systems, at least one service order respectively associated with the at least one of the plurality of medical systems.

4. The system of claim 1, wherein, to issue the at least one warning respectively associated with the at least one of the plurality of medical systems, the instructions further cause the system to provide information indicating the at least one warning via a display of the at least one of the plurality of medical systems.

5. The system of claim 4, wherein the at least one warning is associated with past operation of the at least one of the plurality of medical systems by at least one medical personnel.

6. The system of claim 1, wherein the instructions further cause the system to:

store the first sensor data via a database;

wherein, to search the first sensor data to determine the report data, the instructions further cause the system to search the database to determine the report data.

7. The system of claim 1, wherein, to provide, via the graphical user interface, the report data to the user, the instructions further cause the system to provide at least a portion of a web-based application to the user.

8. At least one non-transitory computer readable storage medium that includes instructions that, when executed by a processor of a system, cause the system to:

receive first sensor data associated with a first plurality of measurements of a plurality of components of a plurality of medical systems;

receive filter information from first user input;

search, based at least on the filter information, the first sensor data to determine report data;

provide, via a graphical user interface, the report data to a user, the report data displayed on the graphical user interface, the report data comprising a plot of data points associated with the first sensor data;

receive second user input that indicates one or more issues associated with at least one of the plurality of medical systems;

determine one or more thresholds based at least on the second user input;

display the one or more thresholds on the graphical user interface, the plot of data points associated with the first sensor data displayed with the one or more thresholds;

receive second sensor data associated with a second plurality of measurements of the plurality of components of the plurality of medical systems;

display a plot of data points associated with the second sensor data on the graphical user interface along with the one or more thresholds;

determine, based at least on the one or more thresholds, at least one of the one or more issues associated with at least one of the plurality of medical systems, at least one of the plotted data points associated with the first sensor data located outside the one or more thresholds indicating an issue with at least one of the plurality of medical systems; and issue, based at least on the at least one of the one or more issues associated with the at least one of the plurality of medical systems, at least one warning respectively associated with the at least one of the plurality of medical systems.

9. The at least one non-transitory computer readable storage medium of claim 8, wherein the instructions further cause the system to:

issue, based at least on the at least one of the one or more issues associated with the at least one of the plurality of medical systems, at least one preventative maintenance order respectively associated with the at least one of the plurality of medical systems.

10. The at least one non-transitory computer readable storage medium of claim 8, wherein the instructions further cause the system to:

issue, based at least on the at least one of the one or more issues associated with the at least one of the plurality of medical systems, at least one service order respectively associated with the at least one of the plurality of medical systems.

11. The at least one non-transitory computer readable storage medium of claim 8, wherein, to issue the at least one warning respectively associated with the at least one of the plurality of medical systems, the instructions further cause the system to provide information indicating the at least one warning via a display of the at least one of the plurality of medical systems.

12. The at least one non-transitory computer readable storage medium of claim 11, wherein the at least one warning is associated with past operation of the at least one of the plurality of medical systems by at least one medical personnel.

13. The at least one non-transitory computer readable storage medium of claim 8, wherein, to provide, via the graphical user interface, the report data to the user, the instructions further cause the system to provide at least a portion of a web-based application to the user.

14. A method, comprising:

receiving first sensor data associated with a first plurality of measurements of a plurality of components of a plurality of medical systems;

receiving filter information from first user input;

searching, based at least on the filter information, the first sensor data to determine report data;

providing, via a graphical user interface, the report data to a user, the report data displayed on the graphical user interface, the report data comprising a plot of data points associated with the first sensor data;

receiving second user input that indicates one or more issues associated with at least one of the plurality of medical systems;

determining one or more thresholds based at least on the second user input;

displaying the one or more thresholds on the graphical user interface, the plot of data points associated with the first sensor data displayed with the one or more thresholds;

receiving second sensor data associated with a second plurality of measurements of the plurality of components of the plurality of medical systems;

displaying a plot of data points associated with the second sensor data on the graphical user interface along with the one or more thresholds;

determining, based at least on the one or more thresholds, at least one of the one or more issues associated with at least one of the plurality of medical systems, at least one of the plotted data points associated with the first sensor data located outside the one or more thresholds indicating an issue with at least one of the plurality of medical systems; and issuing, based at least on the at least one of the one or more issues associated with the at least one of the plurality of medical systems, at least one warning respectively associated with the at least one of the plurality of medical systems.

15. The method of claim 14, further comprising:

issuing, based at least on the at least one of the one or more issues associated with the at least one of the plurality of medical systems, at least one preventative maintenance order respectively associated with the at least one of the plurality of medical systems.

16. The method of claim 14, further comprising:

issuing, based at least on the at least one of the one or more issues associated with the at least one of the plurality of medical systems, at least one service order respectively associated with the at least one of the plurality of medical systems.

17. The method of claim 14, wherein the issuing the at least one warning respectively associated with the at least one of the plurality of medical systems includes providing information indicating the at least one warning via a display of the at least one of the plurality of medical systems.

18. The method of claim 17, wherein the at least one warning is associated with past operation of the at least one of the plurality of medical systems by at least one medical personnel.

19. The method of claim 14, further comprising:

storing the first sensor data via a database;

wherein the searching, based at least on the filter information, the first sensor data to determine the report data includes searching the database to determine the report data.

20. The method of claim 14, wherein the providing, via the graphical user interface, the report data to the user includes providing at least a portion of a web-based application to the user.

* * * * *